United States Patent [19]  
Mahn et al.

[11] Patent Number: 4,724,142  
[45] Date of Patent: Feb. 9, 1988

[54] SYNERGISTIC MICROBIOCIDAL COMPOSITIONS CONTAINING A MIXTURE OF A N-ALKYL DIMETHYLBENZYLAMMONIUM HALIDE AND AN ACROLEIN/FORMALDEHYDE POLYCONDENSATION PRODUCT

[75] Inventors: Frederick R. Mahn, Verona; Lora J. Bogdany, Denville; Joseph J. Baron, Morris Plains; Edward G. Knapick; Edward M. Antonucci, both of Randolph, all of N.J.

[73] Assignee: Drew Chemical Corporation, Boonton, N.J.

[21] Appl. No.: 75,905

[22] Filed: Jul. 20, 1987

Related U.S. Application Data

[63] Continuation-in-part of Ser. No. 894,266, Aug. 6, 1986, abandoned.

[51] Int. Cl.$^4$ .................. A61K 31/765; A01N 33/12  
[52] U.S. Cl. ..................................... 424/82; 514/643  
[58] Field of Search ........................ 424/82; 514/643

[56] References Cited

U.S. PATENT DOCUMENTS 4,173,643 11/1979 Law ........................................ 514/372  
4,501,668 2/1985 Mertz et al. ........................... 210/749

Primary Examiner—Allen J. Robinson  
Attorney, Agent, or Firm—Walter H. Schneider

[57] ABSTRACT

A synergistic microbiocidal composition for inhibiting bacterial growth comprising as Component (1) a polycondensation product of acrolein/formaldehyde in a molar ratio of 1:1–10:1 and as Component (2) an N-alkyl($C_8$–$C_{30}$) dimethylbenzyl ammonium halide, Component (1) and Component (2) being in a weight ratio of about 1:10–10:1.

2 Claims, No Drawings

SYNERGISTIC MICROBIOCIDAL COMPOSITIONS CONTAINING A MIXTURE OF A N-ALKYL DIMETHYLBENZYLAMMONIUM HALIDE AND AN ACROLEIN/FORMALDEHYDE POLYCONDENSATION PRODUCT

This application is a continuation-in-part of application Ser. No. 894,266 filed Aug. 6, 1986, now abandoned.

BACKGROUND OF THE INVENTION

1. Field of the Invention

The present invention relates to inhibiting the growth of bacteria in various industrial environments. More particularly, the present invention relates to an improved microbiocidal composition and its method of use. Still more particularly, the present invention relates to a synergistic microbiocidal composition, and its method of use, the composition comprising a combination of (1) a polycondensation product of acrolein and formaldehyde and (2) an N-alkyldimethylbenzyl ammonium halide.

2. Description of the Prior Art

The presence of organic materials in the manufacture and/or use of various aqueous systems such as latices, adhesives, paints, coatings, mineral slurries and the like renders them susceptible to deterioration by virtue of exposure to bacteria and other microorganisms existing in the particular environment. It is, therefore, a conventional practice to seek to inhibit the microbial deterioration of such systems by incorporating therein any of various materials or combinations of materials that are characterized by having antibacterial activity.

Numerous materials have been found to possess such antibacterial activity. For instance, various quaternary ammonium salts having this activity are disclosed in U.S. Pat. No. 4,479,820; various acrolein/formaldehyde polycondensation products are disclosed in U.S. Pat. No. 4,501,668; and, in addition, U.S. Pat. Nos. 3,231,509 and 4,173,643 disclose microbiocidal synergistic combinations comprising quaternary ammonium salts with, respectively, bis(halomethyl)sulfones and 4-isothiazolin-3-ones.

SUMMARY OF THE INVENTION

It is a principal object of this invention to provide an improved microbiocidal composition. It is a further object of this invention to provide an improved microbiocidal composition that is storage stable, and which is compatible with a variety of systems susceptible to biocidal degeneration thereby permitting its use without objectionable and/or unacceptable by-product odor, discoloration, thickening and the like. A further object of this invention is to provide an improved microbiocidal composition that is cost effective, i.e., performs effectively on the basis of its cost per unit weight and duration of its effectiveness on the treated system. Another object of this invention is to provide an improved method of inhibiting bacterial growth in a variety of systems in industry and commerce.

DESCRIPTION OF THE PREFERRED EMBODIMENT

These objects have been met in accordance with this invention by a composition comprising (1) an acrolein/formaldehyde condensation product having a molar ratio between 1:1 and 1:10 in combination with (2) an N-alkyldimethyl benzyl ammonium halide in which the alkyl group has a carbon chain length of $C_8$ to $C_{30}$.

In accordance with the present invention the acrolein/formaldehyde condensation product (Component 1) is produced by the condensation of acrolein and formaldehyde in a preferred molar ratio of 1:2–1:4 in an aqueous/organic medium in the presence of a basic catalyst. Such a condensation product is available commercially under the trademark Formac® 40 from Degussa.

Preferably, the quaternary ammonium salt (Component 2) is an N-long chain alkyl ($C_{12}$:40%; $C_{14}$:50%; $C_{16}$:10%) dimethylbenzyl ammonium chloride. Such a compound is available commercially under the trademark Hyamine® 3500 from Lonza, Inc.

In the practice of the invention, the acrolein/formaldehyde condensation product (Component 1) and the quaternary ammonium salt (Component 2) will generally be used in a range of 1:10–10:1 parts by weight. It has been observed, however, that the synergism exhibited by the composition, particularly at lower dosages of use, is more pronounced when the condensation product of acrolein/formaldehyde is greater. The composition will preferably be used, therefore, in ratios of 1:1 to 5:1 (Component 1/Component 2), for example, 3:1. The composition can be employed in the form of a dilute aqueous or non-aqueous solution and can be added to the aqueous system to be treated in any conventional way in an amount effective to inhibit microorganic growth. Generally, the effective concentration will range from as little as 100 ppm to as high as 5000 ppm, or higher, depending upon the nature of the system being treated. Usually, a concentration on the order of 500–2000 ppm will be found adequate depending to some extent, of course, upon the ratio of components.

In order to demonstrate the synergistic microbiocidal activity of the composition of this invention, the following Example was conducted. All parts are by weight unless otherwise noted.

EXAMPLE

An unpreserved sample of styrene-butadiene-vinylidene chloride (SBVC) latex was analyzed for microbial content before being utilized for preservation evaluation according to this invention. It was determined that the latex sample was free of contamination.

The uncontaminated, unprotected SBVC latex was divided into 50 gr. aliquots and dosed with the microbiocide composition of this invention as reported in the following Table. Each of Components 1 and 2 was also separately tested as microbiocides while two aliqouts remained untreated to serve as controls.

The challenged inoculum was a pooled suspension of microorganisms comprising the bacteria species Pseudomonas, Bacillus and Penicillium, that had been grown from contaminated latex material. All of the samples were challenged on a weekly basis for 4 weeks with 0.10 ml. of the pooled suspension containing at least $10^6$ organisms per ml. Following 72 hours of room temperature incubation, a one ml. quantity of each sample was transferred to 20 ml. of tryptic soy broth (TSB). The TSB tubes were incubated at room temperature for 24 hours and streaked onto TGE plates for growth bacteria. After 48 hours incubation at room temperature, the plates were read and graded according to the description following the Table.

The tested compositions comprised combinations of Component 1 and Component 2 in varying ratios. Component 1 was the above identified commercially available Formac ® 40 obtained as an aqueous solution containing 40% active ingredient. Component 2 was the above identified Hyamine ® 3500 obtained as an aqueous solution containing 80% active ingredient. The compositions of this invention as well as the separately tested components were adjusted to an active ingredient content of 20%.

Results appear in the following Table.

TABLE

| Biocide | Ratio | PPM | Weekly Growth Rate* | | | |
|---|---|---|---|---|---|---|
| | | | 1 | 2 | 3 | 4 |
| Components 1 and 2 | 1:3 | 500 | — | +1 | +1 | +1 |
| | | 1000 | — | — | — | — |
| | | 2000 | — | — | — | — |
| | 1:1 | 500 | — | +1 | +1 | +1 |
| | | 1000 | — | +1 | +1 | +1 |
| | | 2000 | — | — | — | — |
| | 3:1 | 500 | — | — | — | — |
| | | 1000 | — | — | — | — |
| | | 2000 | — | — | — | — |
| Component 1 | | 500 | +1 | +1 | +1 | +2 |
| | | 1000 | — | +1 | +1 | +1 |
| | | 2000 | — | +1 | +1 | +1 |
| Component 2 | | 500 | +4 | +4 | +4 | +4 |
| | | 1000 | +4 | +4 | +4 | +4 |
| | | 2000 | +4 | +4 | +4 | +4 |
| Control #1 | | | +2 | +4 | +4 | +4 |
| Control #2 | | | +4 | +4 | +4 | +4 |

*The rating system for microbial growth on streaked, prepoured agar plates is as follows:

| Growth rate | Description |
|---|---|
| — | No growth; zero colonies |
| +1 | Maximum of 15 total colonies with no more than 5 of these having diameters of ⅛ inch |
| +2 | Sporadic growth on ¼ total streaked area, remaining ¾ area relatively clear; maximum of 20 total colonies with no more than 6 of these having diameters greater than ⅛ inch |
| +3 | Dense growth on ½–¾ of streaked area; minor colonies too numerous to count; 20 or more major colonies having diameters of ⅛ inch or larger |
| +4 | Uniform, dense growth over entire streaked area; colonies pinhead size or larger |

Reference in the disclosure to details of specific embodiments is not intended to restrict the scope of the appended claims, which themselves recite those features regarded as essential to the invention.

We claim:

1. A microbiocidal composition comprising a synergistic mixture the first component of which is an acrolein/formaldehyde polycondensation product having a molar ratio of 1:2–1:4 and the second component of which is an N-alkyl ($C_{12}$:40%; $C_{14}$:50%; $C_{16}$:10%) dimethylbenzyl ammonium chloride, said first and second components being in a ratio of 1:3–3:1 by weight.

2. A method for inhibiting the growth of bacteria in an aqueous system which comprises adding to said system an amount of a microbiocidal composition according to claim 1 effective to inhibit the growth of bacteria.

* * * * *